United States Patent [19]

Schulz et al.

[11] Patent Number: 5,639,901
[45] Date of Patent: Jun. 17, 1997

[54] ORGANOSULFUR GOLD COMPOUNDS, A PROCESS FOR THEIR PRODUCTION AND THEIR USE

[75] Inventors: Andreas Schulz, Neu-Isenburg; Marco Höfler, Freigericht, both of Germany

[73] Assignee: Cerdec Aktiengesellschaft Keramische Farben, Frankfurt, Germany

[21] Appl. No.: 390,483

[22] Filed: Feb. 17, 1995

[30] Foreign Application Priority Data

Feb. 21, 1994 [DE] Germany ................ 44 05 424.6

[51] Int. Cl.$^6$ .................. C07F 1/12; B05D 5/10
[52] U.S. Cl. ............... 556/113; 427/208.2; 427/229; 427/428; 427/429
[58] Field of Search .......... 556/113; 427/208.2, 427/229, 428, 429

[56] References Cited

U.S. PATENT DOCUMENTS

| 5,162,556 | 11/1992 | Maeda et al. | 556/113 |
| 5,235,079 | 8/1993 | Lotze et al. | 556/113 |
| 5,252,764 | 10/1993 | Lotze et al. | 556/113 |
| 5,491,247 | 2/1996 | Gernon | 556/113 |

FOREIGN PATENT DOCUMENTS

| 9 481 143 | 6/1992 | European Pat. Off. . |
| 0 491 147 | 6/1992 | European Pat. Off. . |
| 0 514 073 | 11/1992 | European Pat. Off. . |
| 3 217 049 | 11/1982 | Germany . |
| 2 216 536 | 10/1989 | United Kingdom . |

Primary Examiner—Porfirio Nazario-Gonzalez
Attorney, Agent, or Firm—Wenderoth, Lind & Ponack

[57] ABSTRACT

Various organosulfur gold compounds and their use for the production of gold decorations are known.

The invention relates to new organosulfur gold compounds, to a process for their production and to their use for the production of preparations for producing a gold decoration on firing-resistant substrates.

The gold compounds according to the invention are obtainable from monogold(I) dimercaptosuccinic acid and compounds of similar structure by dissolution thereof in water in the presence of a base and precipitation by acidification and, if desired, repetition of the dissolving and precipitating steps. The gold compounds according to the invention are characterized by a gold content of 60 to 90% by weight, an atomic ratio of greater than 0.7 to 4. Preferred gold compounds are soluble in water and are suitable as a constituent of organic/aqueous and exclusively aqueous bright and burnished gold preparations for the decoration of glass, porcelain and ceramic.

12 Claims, 2 Drawing Sheets

ORGANOSULFUR GOLD COMPOUNDS, A PROCESS FOR THEIR PRODUCTION AND THEIR USE

DESCRIPTION

This invention relates to new organosulfur gold compounds and to a process for their production. The invention also relates to the use of the new compounds for the production of preparations for producing a gold decoration on firing-resistant substrates.

Gold preparations, including so-called bright gold preparations and burnished gold preparations, have long been used for the production of gold decorations, including conductors of integrated circuits, on firing-resistant substrates, such as in particular, glass, porcelain and ceramic. Preparations of the type in question generally contain one or more organosulfur gold compounds, one or more organic polymeric binders and a solvent system. The preparations additionally contain other soluble and/or insoluble noble metal compounds and/or gold and one or more fluxes for establishing required optical and performance properties of the decoration to be produced and also other auxiliaries for establishing the processing properties of the preparations. The noble metal preparations are applied to the surface to be coated by conventional direct and indirect printing processes, spraying or brushing or by the transfer technique. Evaporation of the solvent is followed by a firing step at a temperature adapted both to the substrate and to the gold preparation. The maximum firing temperature is mostly between 400° and 900° C., although even higher temperatures may be applied in special cases. A noble metal film is formed and fixed on the surface of the substrate by the firing operation.

For some time, the organosulfur gold compounds used for the decorative preparations mentioned have been almost exclusively so-called gold sulforesinates obtained from a gold(III) salt and a sulfurized, more particularly naturally occurring terpene. In these gold sulforesinates and also in synthetic gold thiolates corresponding to the general formula Au—S—R, where R is an alkyl, cycloalkyl, aryl or aralkyl group or a bicyclic hydrocarbon radical, the gold is present in its monovalent form. When used in gold preparations, the gold compounds mentioned above require the use of an exclusively organic solvent system.

For industrial hygiene, safety and ecological reasons, there is a growing interest in noble metal preparations for decorating firing-resistant substrates in which the organic solvent of the solvent system is at least partly replaced by water. Thus, DE-OS 32 17 049 describes a coating composition for applying an overglaze decoration to porcelain which contains 15 to 40% by weight of polyvinyl pyrrolidone or a mixture of polyvinyl pyrrolidone and aqueous polyethylene oxide, 45 to 85% by weight of ethylene glycol and/or propylene glycol and optionally water. The document in question mentions oxides, gold and organic gold compounds as coloring constituents but does not disclose a single structure of the gold compounds.

EP-A 0 514 073 describes homogeneous compositions, preferably solutions, which form a glossy metallic noble metal film on firing. The compositions contain 3 to 22% by weight of a noble metal thiolate, a polymeric resin and, as solvent system, a mixture of water and an organic solvent (co-solvent) which is preferably a water-miscible alcohol, ether or ester. Both the noble metal thiolate and the binder are said to be soluble in the water/co-solvent mixture. The gold(I) thiolates preferably used are those corresponding to the general formula Au—S—R—H or Au—S—R—X, where X is a nitro group or —COOH, —SO$_2$OH, —OH, —CONH$_2$, —NH$_2$ or —O—P(O)(OH)$_2$, the hydrogen atoms optionally being substituted, or salts thereof and R is a divalent organic radical. It is clearly apparent from the many Examples and Comparison Examples in the cited document that only very special gold(I) thiolates in corresponding gold preparations containing water and co-solvent lead to decorations which combine high gloss with firm adhesion to the decorated substrate. By contrast, only dull and/or poorly adhering decorations are obtained with other gold(I) thiolates corresponding to the above formulae.

Accordingly, the problem addressed by the present invention was to provide a new group of sulfur-containing gold compounds which would be suitable for use in water-containing preparations for producing gold decorations, more particularly high-gloss gold decorations.

It has been found that, after dissolution in water in the presence of a base, preferably an amine, and subsequent acidification, monogold(I) dimercaptosuccinic acid and organosulfur gold compounds of similar structure are not precipitated in the form of the original compound, but surprisingly in the form of completely new organosulfur gold compounds. The new organosulfur gold compounds obtainable as outlined above are soluble in water in the presence of a base. Water-soluble organosulfur gold compounds according to the invention can be directly obtained from the resulting solutions.

The organosulfur gold compounds according to the invention are characterized by a gold content of 60 to 90% by weight and an atomic ratio of gold to sulfur of greater than 0.7 to 4. The organosulfur gold compounds according to the invention are obtainable by the process described hereinafter. The gold compounds preferably have a gold content of 68 to 85% by weight and more particularly 73 to 80% by weight and an atomic ratio of gold to sulfur of greater than 1 to 3:1 and more particularly 1.2 to 2:1 and are readily soluble in water, optionally after the addition of a base.

The new organosulfur gold compounds have properties which distinguish them fundamentally from the starting compounds used for their production. Thus, the new compounds cannot be electrochemically reduced up to −1.8 volts. This is surprising because gold(I) thiolates, such as the gold(I) mercaptopropionyl glycine and gold(I) mercaptosuccinic acid mentioned in EP-A 0 514 073, show a halfwave reduction potential of −550 mV against silver/silver chloride, as polarographically determined in 0.05-molar sodium hydroxide. The monogold(I) dimercaptosuccinic acid particularly suitable for the production of the new gold compounds is also easy to reduce electrochemically—halfwave potential in 0.5-molar sodium hydroxide −700 mV against Ag/AgCl. The electrochemical non-reducibility of the new gold compounds by comparison with gold(I) thiolates is an indication that the new compounds are not gold(I) thiolates, but Au compounds with a valency of the gold of lower than +1. FIG. 1 shows the voltammogram of the gold compound of Example 3 according to the invention while FIG. 2 for comparison shows the voltammogram of the starting compound of Example 1 (it is important to note that the ordinate in FIG. 1 shows nA while the ordinate in FIG. 2 shows μA). The maximum of the Au4f$_{7/2}$ peak of monogold(I) dimercaptosuccinic acid and of the organosulfur gold compound according to the invention produced therefrom (Example 3) was determined in comparison with elemental gold by X-ray photoelectron spectroscopy/XPS/ESCA (high spectrometer resolution) using a sputtered high-purity gold sample as the calibration standard. At 84.2 eV, the maximum of the above-mentioned peak of the compound according to the invention lies between the values for metallic gold (84.0 eV) and the gold (I) thiolate used as starting material (Example 1) (84.46 eV). The small, but significant signal shift of the Au4f$_{7/2}$ peak towards higher binding energies compared with metallic gold is regarded as an indication of the presence of a gold cluster with a valency of the gold of lower than +1 and higher than 0. The very high gold content and the high atomic ratio of Au to S may be regarded as further indications of this. The starting compounds also differ basically from the compounds according to the invention in their IR spectra, FIG. 3 showing the IR spectrum of the product of Example 3 and FIG. 4 the IR spectrum of the starting product (Example 1).

The gold compounds according to the invention may be produced by a process comprising the following steps:

(i) dissolving a monogold(I) dimercaptocarboxylic acid compound corresponding to general formula (A):

(A)

in which Q is an aliphatic $C_{2-4}$ alkane tetrayl radical or a 5- or 6-membered cycloaliphatic tetrayl radical optionally containing an oxygen or imine ring member and Y is hydrogen or COOH and the S atoms are positioned at adjacent carbon atoms, or a salt of compound (A) in water in the presence of a base, preferably an amine, (ii) adding a mineral acid to the solution of stage (i) to a pH value of 2 or lower and (iii) isolating the product precipitated in stage (ii).

The group Y is preferably a carboxyl group. Accordingly, particularly preferred monogold(I) dimercaptocarboxylic acid starting materials corresponding to formula (A) are monogold(I) dimercaptosuccinic acid, monogold(I)-2,3-dimercaptoglutaric acid and monogold(I)-2,3- or -3,4-dimercaptoadipic acid. Monogold(I)-3,4-dimercapto-2,5-dicarboxylic acid and monogold(I)-2,3-dimercaptocyclohexane-1,4-dicarboxylic acid are mentioned as examples of the cyclic starting compounds corresponding to formula (A). The monogold(I) dithiolates corresponding to formula (A) used as starting compounds are prepared in basically the same way as known to experts from the production of known noble metal thiolates: a gold(I) complex corresponding to the formula AuCl(RSR') is formed from tetrachloroauric acid after addition of twice the equivalent quantity of a thioether corresponding to the formula RSR'; according to EP-B 0 491 147, a particularly suitable thioether for this reaction is methionine. The complex mentioned is then reacted with a substantially equivalent molar quantity of the dithiol (dimercapto compound) on which compound (A) is based in the presence of a solvent, resulting in the formation of the monogold compound corresponding to formula (A). The production of the dithiol compound on which compound (A) is based comprises standard process steps: for example, dimercaptoalkane dicarboxylic acids can be obtained by reacting the corresponding alkine dicarboxylic acids with thioacetic acid; another possible method of obtaining aliphatic and cyclic dimercapto compounds on which the gold compounds of formula (A) are based is to react the corresponding dihalogen compound (Y—Q(Hal)$_2$—COOH) with an alkali metal sulfide.

Any base, such as for example sodium hydroxide or an amine, may be used in step (i) of the process according to the invention. Preferred bases are amines, including primary, secondary and tertiary amines with aliphatic, cycloaliphatic and/or aromatic radicals and also N-heterocyclic bases, such as in particular pyridine. Tertiary amines with identical or different lower ($C_{1-4}$) alkyl radicals are preferred, triethylamine, tri-n-propylamine and triisopropylamine being particularly preferred. In step (i), the gold compound is introduced into water and a base, preferably an amine, is added in such a quantity that the gold compound dissolves. If a water-soluble salt of the monogold(I) dimercaptocarboxylic acid compound corresponding to general formula (A) is directly used in step (i), there is no need to add a base or the quantity of base added may optionally be reduced. Using the monogold compound corresponding to general formula (A), a pH value of at least 8 and preferably a pH value of 9 to 14 is best adjusted by addition of the base. The monogold compound corresponding to general formula (A) is preferably used in such a quantity that a gold content of 2 to 20% by weight is obtained in the solution.

A mineral acid, preferably hydrochloric acid, is added in step (ii) until a pH value of 2 or lower is reached. A brown to black product precipitates during or after addition of the mineral acid and is removed from the solution in known manner in step (iii).

The product isolated in step (iii) already has all the properties of the organosulfur gold compounds according to the invention. A further increase in the gold content and reduction in the sulfur content can be obtained by repeating steps (i) to (iii) one or more times, preferably once or twice, the product isolated in step (iii) of the preceding sequence being used as the starting product for step (i) of the second and following sequences. Steps (i) to (iii) may be carried out at room temperature or at elevated temperatures, preferably at 30° to 80° C.

The organosulfur gold compounds obtainable by the described process dissolve in water in the presence of a base. Water-soluble organosulfur gold compounds with the properties characteristic of the new class of compounds are directly obtained by evaporation of the water from the resulting solution under reduced pressure.

It has been found that the organosulfur gold compounds according to the invention are eminently suitable for the production of a gold decoration on firing-resistant substrates, such as in particular glass, porcelain and ceramic. To produce a gold decoration, the organosulfur gold compounds are best not used as such, but in the form of preparations containing them, more particularly in the form of so-called bright gold and burnished gold preparations, and in the form of transfers of which the decorative layer contains the organosulfur gold compounds and organic polymeric binders.

The preparations mentioned, including so-called bright gold and burnished gold preparations, for producing a gold decoration on a firing-resistant substrate or for producing the decorative layer of a transfer contain at least one organosulfur gold compound according to the invention, one or more polymeric organic binders and a solvent system which dissolves the polymers and the gold compound or otherwise guarantees a uniform distribution. If necessary, the preparations in question additionally contain other noble metal compounds in the form of simple salts, complexes, resinates or thiolates of silver, platinum and/or palladium to adjust color tones of the required decoration. Burnished gold preparations additionally contain gold powder and/or insoluble gold compounds. In addition, the preparations generally contain fluxes in the form of compounds, for example resinates, salts, oxides or coordination compounds, of one or more of the elements boron, silicon, vanadium, chromium, indium, tin, antimony, bismuth or rhodium and other auxiliaries to obtain the required process properties, for example a screen-printable viscosity and/or a high drying rate of the preparation, and to establish specific optical and performance properties, such as firm adhesion of the fired decoration to the substrate.

The organosulfur gold compounds according to the invention may be used in preparations of which the solvent system is exclusively organic, organic/aqueous or exclusively aqueous. The expert will coordinate the binders and solvents to be used in the preparations with one another to obtain a homogeneous composition, preferably a solution.

Aqueous/organic or exclusively aqueous preparations containing an organosulfur gold compound according to the invention contain polymeric binders which are soluble in water or which form a clear dispersion therein. Useful binders are polyacrylic acid, polymethacrylic acid, polyvinyl pyrrolidone, cellulose ethers, more particularly carboxyalkyl and hydroxyalkyl cellulose, polyalkylene glycol, polyvinyl acetate, polyvinyl alcohol, polyamines, alkyd resins and polyurethane resins. The binders may be used in the form of homopolymers or copolymers or block polymers either individually or in the form of mixtures. In a particularly preferred embodiment, polyvinyl pyrrolidone homopolymers or copolymers, polymethacrylic acid homopolymers or copolymers and resins based on cellulose ethers are used for purely aqueous preparations or for preparations of high water content.

Preparations with an aqueous/organic binder system contain one or more water-soluble organic solvents, more particularly water-soluble alcohols, ethers and esters, as the organic solvent. Glycols containing 2 to 4 carbon atoms and oligo- and poly-$(C_{2-4})$glycols or mono$(C_{1-4})$alkyl ethers of the glycols or oligoglycols mentioned are particularly preferred, as are hydroxycarboxylic acids or lower alkyl esters thereof, such as in particular $C_{1-3}$ alkyl lactate.

As already discussed, it is surprisingly also possible using the organosulfur gold compounds according to the invention to produce substantially aqueous preparations (organic solvent content less than 1% by weight) by dissolving the gold compound according to the invention in water, if necessary after addition of an amine, and combining the resulting solution in known manner with an aqueous solution or emulsion containing water-soluble organic binders and other auxiliaries. To obtain particularly high-gloss gold decorations, the aqueous preparations in question best additionally contain an effective quantity, generally 0.01 to 2.0% by weight, of an anionic, cationic, zwitterionic or nonionic surfactant. Extremely effective surfactants are polyether-modified dimethyl polysiloxanes and alkyl benzene sulfonates.

Other auxiliaries in the preparations according to the invention may be typical substances for varying the rheological properties of the preparation, surfactants, adhesion-strengthening auxiliaries and drying accelerators where a UV-curable resin is used. In some cases, the additional use of an aqueous polysulfide solution has proved useful.

Aqueous and aqueous/organic bright gold preparations containing at least one organosulfur gold compound according to the invention contain this organosulfur gold compound in a quantity of 2 to 25% by weight and preferably 5 to 15% by weight, expressed as gold. The percentage binder content of the preparations is generally between 5 and 45% by weight, the ratio by weight of resin to noble metal preferably being between 0.5:1 and 1.5:1. The water content is generally between 10 and 90% by weight and preferably between 30 and 70% by weight while the organic solvent content is between 0 and 40% by weight, based on the preparation. The quantity of flux used is typically between 0.01 and 2% by weight, based on the preparation. So-called burnished preparations additionally contain gold powder and/or fine-particle inorganic insoluble gold compounds. Depending on the required effect, burnished gold preparations may additionally contain glass frits and/or organosilicon compounds.

The preparations containing at least one organosulfur gold compound may be directly applied to the surface to be decorated by conventional decoration processes, such as spraying, brushing and known printing processes, more particularly screen printing processes, and—after evaporation of the solvent constituents—the decoration may be fired at a temperature of generally 400° to 900° C.

A decoration technique widely used in the ceramic industry is based on the use of transfers. Accordingly, the organosulfur gold compounds according to the invention may also be used in the decorative layer of transfers. The transfer is produced in known manner: a decorative layer substantially corresponding in its composition to that used in the preparations described above is applied to a water-soluble separation layer disposed on a substrate or to a thermo-separation layer. After evaporation of the solvent, i.e. essentially water in the case of the preferred preparations, and—if necessary—crosslinking of the binder, the decorative layer is normally covered with a film.

The invention provides a totally new class of organosulfur gold compounds which may be used not only in conventional organic or organic/aqueous preparations for producing gold decorations on firing-resistant substrates, but also in substantially aqueous preparations. Using the new organosulfur gold compounds in aqueous preparations, it is possible to produce high-gloss, firmly adhering gold decorations. Aqueous preparations such as these overcome the disadvantages inevitably attending the use of preparations containing organic solvents.

EXAMPLE 1

Preparation of monogold(I) dimercaptosuccinic acid (Au(I)-dmsa) (starting compound for the production of gold compounds according to the invention)

0.035 mole=18.49 g of $HAuCl_4$ (37.29% Au) is added dropwise with stirring to a suspension of 0.07 mole of methionine in 70 ml of $H_2O$. The temperature is kept at 0° to 5° C. by external cooling. On completion of the reaction, the gold(I) complex is added dropwise over a period of 1 hour to a suspension of 0.035 mole=6.38 g of meso-2,3-dimercaptosuccinic acid in 150 ml of dichloromethane. The precipitate is filtered under suction, washed repeatedly with water and dried in vacuo over blue gel in an exsiccator. The yield of monogold dimercaptosuccinic acid is 96.5%, based on the gold used.

| Analysis: | Au | C | H | S |
|---|---|---|---|---|
| Calculated: | 52.09% | 12.70% | 1.33% | 16.96% |
| Found: | 50.81% | 12.05% | 1.52% | 15.62% |

$^{13}$C-NMR in $D_2O$ + trimethylamine δ/ppm 52.58 (CH), 60.95 (CH), 180.64 ($CO_{2-}$) and 182.51 ($CO_{2-}$)

Figure 2:
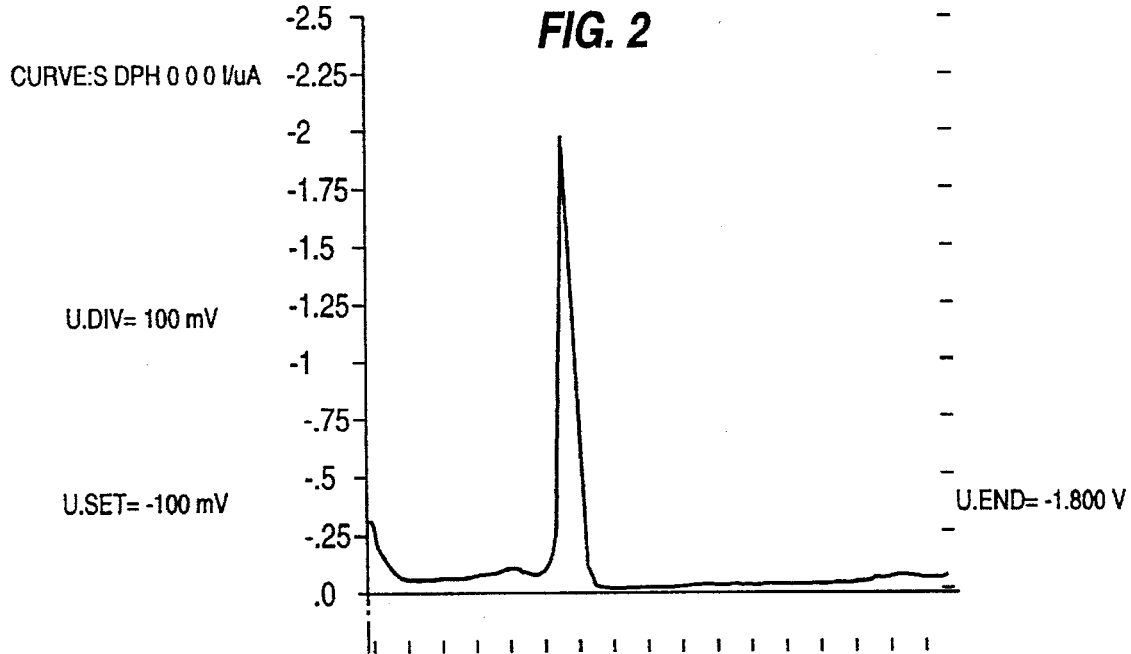
FIG. 2 shows the voltammogram of the starting compound of Example 1.

FIG. 2 shows the voltammogram of Au-dmsa (in 0.05 N KOH) from polarographic determination at an Hg dropping electrode against Ag/AgCl as the reference electrode. The abscissa extends from −100 mV to −1800 mV while the ordinate shows the current in μA (micro A). The curve shows that $Au^{+1}$ is reduced to $Au^0$ at −700 mV.

Figure 4:
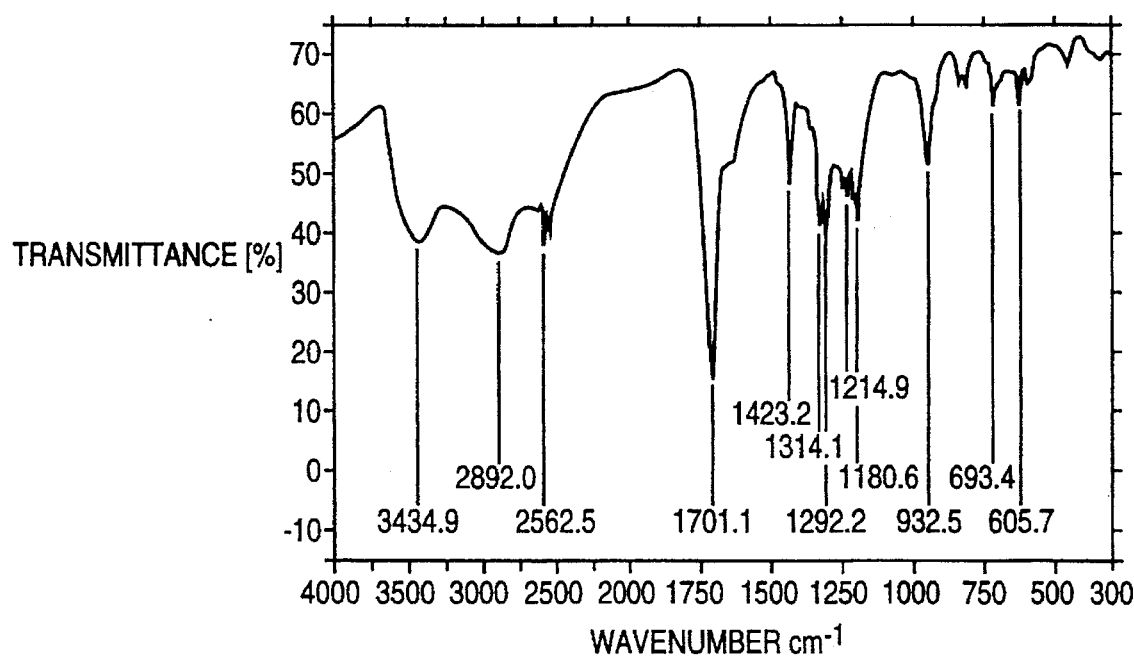
FIG. 4 shows the IR spectrum of the starting product of Example 1.

FIG. 4 shows the IR spectrum of monogold(I) dimercaptosuccinic acid (in a KBr tablet).

From the XPS-ESCA X-ray photoelectron spectrum (instrument: Leybold MAX 100) of Au(I)-dmsa, the maximum of the $Au4f_{7/2}$ peak is 84.46 eV.

EXAMPLE 2

6 g of Au(I)-dmsa from Example 1 are dissolved in 20 ml of water and approx. 3 g of triethylamine at 60° C. The solution is then adjusted to pH 2 with conc. HCl. The precipitate formed is filtered off under suction and washed with water. The filter residue is dried.
Yield: 2.6 g of black substance
Analysis:
Au 68.34%
C 9.07%
H 1.42%
S 10.74%
N 0.55%
Atomic ratio Au:S=1.04:1

For comparison, Au(I)-dmsa contains 52.09% Au and has an Au:S atomic ratio of 0.5.

EXAMPLE 3

2.1 g of the product of Example 2 are dissolved in 15 ml of water and triethylamine at 60° C. The solution is then adjusted to pH 2 with conc. HCl. The precipitate formed is filtered off under suction and washed with water. The filter residue is dried.
Yield: 0.88 g of black substance
Analysis:
Au 73.99%
C 7.12%
H 1.20%
S 10.04%
N 0.57%
Atomic ratio Au:S=1.20:1

Figure 1:
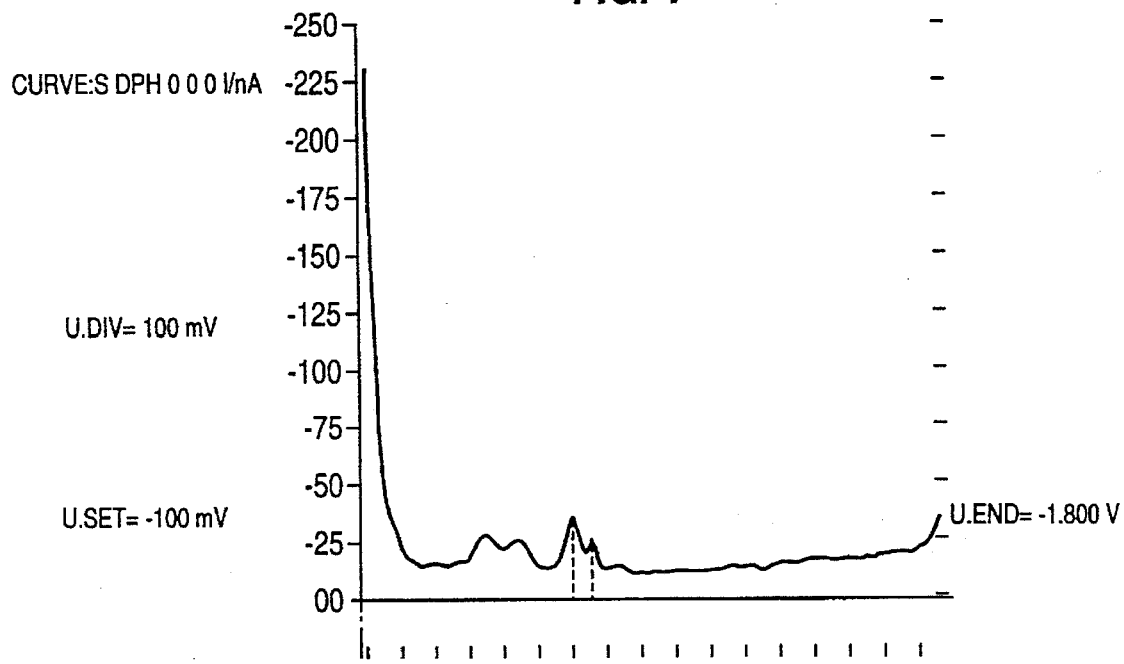
FIG. 1 shows the voltammogram of the gold compound of Example 3.

FIG. 1 shows the voltammogram of the product obtained in Example 3 (in 0.05N NaOH) from polarographic determination at an Hg dropping electrode against Ag/AgCl as the reference electrode. Abscissa from −100 mV to −1800 mV; ordinate in nA (nano-A). The curve shows that, apart from minimal impurities between −400 and −800 mV, no reduction occurs up to −1800 mV.

Figure 3:
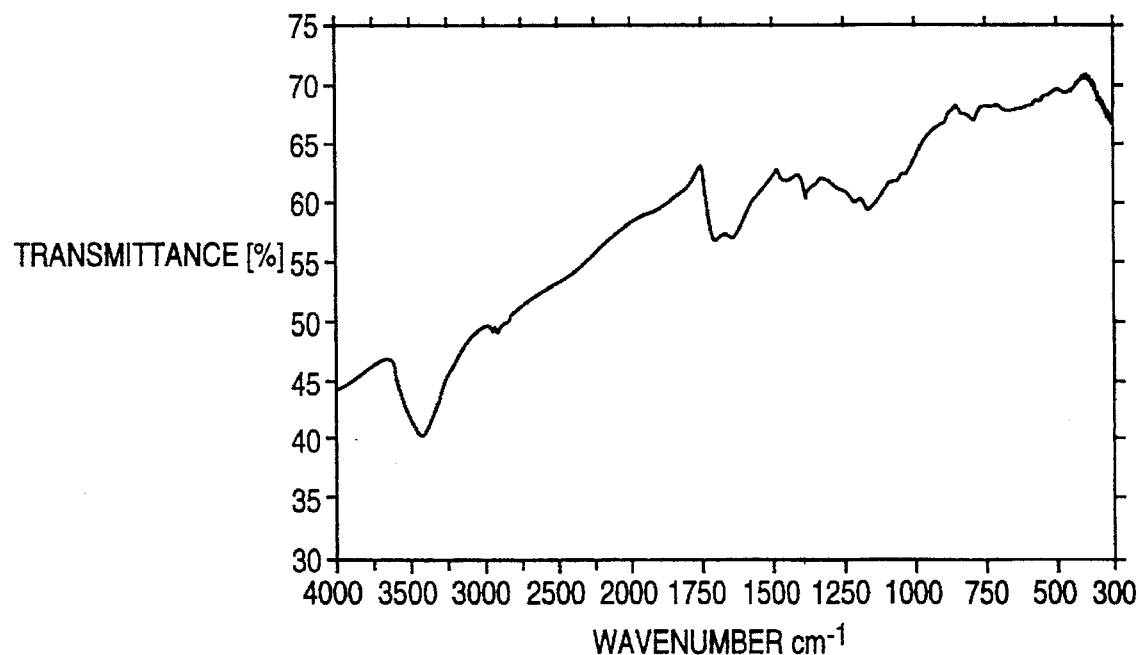
FIG. 3 shows the IR spectrum of the product of Example 3.

FIG. 3 shows the IR spectrum of the product of Example 3 which is completely different from that of the starting product (FIG. 4).

From the XPS-ESCA X-ray photoelectron spectrum (instrument: Leybold MAX 100), the maximum of the $Au4f_{7/2}$ peak is 84.2 eV (for comparison: Au(I)-dmsa 84.46 eV, Au metal 84.0 eV). Quantitative evaluation of the XPS spectrum, which only covers the uppermost atomic layers of the material, produces the following analysis:
O 12.79 atom-%
C 49.68 atom-%
S 13.82 atom-%
Au 23.72 atom-%

EXAMPLE 4

50 g of Au(I)-dmsa are dissolved in 400 ml of water and a corresponding quantity of triethylamine at room temperature so that a pH value above 10 is established in the solution. The solution is then adjusted to pH 2 with conc. HCl. The precipitate formed is filtered and dissolved in water and triethylamine at room temperature, a pH value of 10 being established. The solution was then acidified to pH 2 with conc. HCl. The precipitate is filtered and dried.
Yield: 21.42 g of black substance
Analysis:
Au 70.40%
C 8.25%
H 1.30%
S 10.58%
N 0.74%
Atomic ratio Au:S=1.08:1

EXAMPLE 5

7 g of the compound of Example 4 are dissolved in 25 ml of water and a corresponding quantity of triethylamine at room temperature. The solution was then acidified to pH 1–2 with conc. HCl. The precipitate is filtered and dried.
Yield: 6.15 g black substance
Analysis:
Au 77.28%
C 6.25%
H 0.95%
S 10.25%
N 0.69%
Atomic ratio Au:S=1.23:1

EXAMPLE 6

10 g Of Au(I)-dmsa (26 mmoles) are dissolved in 200 ml of water and 8 g of triethylamine (79 mmoles) at room temperature. 6.6 ml of conc. HCl (approx. 79 mmoles) are then added to the resulting solution. The precipitate formed is filtered and dried.
Yield: 7.83 g of brown substance
Analysis:
Au 60.90%
C 11.45%
H 1.62%
S 12.57%
N 0.50%
Atomic ratio Au:S=0.78:1

EXAMPLE 7

5 g of the product of Example 6 (contains 15 mmoles of Au) are dissolved in 100 ml of water and 4.5 g of triethylamine (45 mmoles) at 60° C. 3.8 ml of conc. HCl (approx. 45 mmoles) are then added to the resulting solution. The precipitate formed is filtered and dried.
Yield: 3.43 g of black substance
Analysis: Au 74.28%

The beginning of the thermodynamic decomposition of the black substance is at 173° C. and is then distinctly below the beginning of decomposition of Au(I)-dmsa (194° C.).

EXAMPLE 8

Bright Gold Preparation

The following constituents were mixed:

| | Parts |
|---|---|
| Polyvinyl pyrrolidone (PVP K25, a product of Fluka) | 5.2 |
| Gold compound of Example 4 | 13.4 |
| Propane-1,2-diol | 6.1 |
| Water | 41.9 |
| Ethyl lactate | 25.1 |
| n-Butanol | 0.9 |
| Rhodium complex | 0.12 |
| Chromium sulfate | 0.33 |
| Ammonium bismuth citrate | 0.44 |
| Triethylamine | 4.4 |
| Ammonium polysulfide*) | 2.1 |

*)15% by weight aqueous solution; same also applies to Examples 9 and 10.

The preparation is applied by screen printing to porcelain and heated for 10 minutes at 820° C., the heating-up time being 1 h. A glossy, firmly adhering film is obtained.

EXAMPLE 9

Bright Gold Product

The following constituents were mixed:

| | Parts |
|---|---|
| PVP K25 | 8.3 |
| Gold compound of Example 5 | 12.6 |
| Propane-1,2-diol | 8.3 |
| Water | 43.4 |
| Ethyl lactate | 16.6 |
| Rhodium complex | 0.15 |
| Chromium sulfate | 0.04 |
| Ammonium bismuth citrate | 0.49 |
| Triethylamine | 5.5 |
| Ammonium polysulfide*) | 2.0 |
| Silver mercaptopropionyl glycine | 2.6 |

*)15% by weight aqueous solution; the same also applies to Examples 9 and 10.

The preparation is applied by screen printing to porcelain and heated for 2 minutes at 880° C., the heating-up time being 30 minutes. A glossy, firmly adhering film is obtained.

EXAMPLE 10

Bright Gold Preparation

The following constituents were mixed:

| | Parts |
|---|---|
| PVP K25 | 5.2 |
| Gold compound of Example 4 | 13.3 |
| Water | 73.3 |
| Rhodium complex | 0.12 |
| Chromium sulfate | 0.33 |
| Ammonium bismuth citrate | 0.43 |
| Triethylamine | 5.2 |
| Ammonium polysulfide*) | 2.1 |

*)15% by weight aqueous solution; the same also applies to Examples 9 and 10.

The preparation is brushed onto porcelain or applied by screen printing and heated for 10 minutes at 820° C., the heating-up time being 1 h. A glossy, firmly adhering film is obtained.

EXAMPLE 11

Preparation of a gold compound according to the invention from monogold(I) dimercaptosuccinic acid (Au(I)-dmsa).

Au(I)-dmsa with an Au content of 52.09% is dissolved in water with addition of tetraethyl ammonium hydroxide. After addition of conc. HCl, a gold compound containing 62.89% precipitates (11/1). By corresponding dissolution of the product 11/1 and precipitation, the Au content is increased to 68.63% (11/2) and, by dissolution of 11/2 and precipitation, to 74.68% (11/3). The gold-to-sulfur ratio increases from 0.54:1 to 0.89:1 (=11/1), then to 1.11:1 (=11/2) and finally to 1.25:1 (=11/3).

A bright gold preparation equivalent to Example 8 but with the Au-compound 11/3 instead of the Au-compound of Example 4 was tested. An attractive firmly adhering, high-gloss film was obtained.

EXAMPLE 12

Au(I)-dmsa is initially dissolved in water with addition of 2 mmoles of triethylamine per mmole of Au(I)-dmsa, 3 mmoles of tetramethyl ammonium chloride are then added. After addition of conc. HCl, a gold compound according to the invention containing 71.31% Au precipitates; the Au:S ratio increases from 0.54 to 1.08:1.

A bright gold preparation equivalent to Example 9 but with the Au-compound of the Example 12 instead of that of Example 5 was tested. An attractive, firmly adhering, high-gloss gold film is obtained.

We claim:

1. An organosulfur gold compound with a gold content of 60 to 90% by weight and an atomic ratio of gold to sulfur of greater than 0.71 to 4:1 obtainable by a process comprising the following steps:

(i) dissolving a monogold(I) dimercaptocarboxylic acid compound corresponding to general formula (A):

in which Q is an aliphatic $C_{2-4}$ alkane tetrayl radical or a 5- or 6-membered cycloaliphatic tetrayl radical optionally containing an oxygen or imine ring member and Y is hydrogen or COOH and the S atoms are positioned at adjacent carbon atoms, or a salt of compound (A) in water in the presence of a base, (ii) adding a mineral acid to the solution of stage (i) to a pH value of 2 or lower and (iii) isolating the product precipitated in stage (ii).

2. An organosulfur gold compound as claimed in claim 1, characterized in that it is soluble in water, optionally after addition of a base.

3. An organosulfur gold compound as claimed in claim 1 or 2, characterized in that it contains 68 to 85% by weight of gold and has an atomic ratio of gold to sulfur of greater than 1 to 3:1.

4. A process for the production of an organosulfur gold compound having a gold content of 60 to 90% by weight and an atomic ratio of gold to sulfur of greater than 0.71 to 4:1 which comprises:
   (i) dissolving a monogold (I) dimercaptocarboxylic acid compound corresponding to general formula (A):

in which Q is an aliphatic $C_{2-4}$ alkane tetrayl radical or a 5-or 6-membered cycloaliphatic tetrayl radical optionally containing an oxygen or imine ring member and Y is hydrogen or COOH and the S atoms are positioned at adjacent carbon atoms, or a salt of compound (A) in water in the presence of a base,
   (ii) adding a mineral acid to the solution of stage (i) to a pH value of 2 or lower and
   (iii) isolating the product precipitated in stage (ii).

5. A process as claimed in claim 4, wherein steps (i) to (iii) are carried out one or more times, the product isolated in step (iii) of the preceding sequence being used as the starting product for step (i) of the second and following sequences.

6. A process as claimed in claim 4 or 5, wherein an amine and/or a tetraalkyl ammonium hydroxide is used as the base.

7. A process as claimed in claims 4 or 5, wherein an aqueous solution of the gold compound of formula A, which contains tetraalkyl ammonium ions through the addition of tetraalkyl ammonium hydroxide or a tetraalkyl ammonium salt, is employed in step (ii).

8. A process as claimed in claim 6, wherein an aqueous solution of the gold compound of formula A, which contains tetra-alkyl ammonium ions through the addition of tetraalkyl ammonium hydroxide or a tetraalkyl ammonium salt, is employed in step (ii).

9. A process as claimed in claim 4 or 5, wherein, in step (i), monogold (I) dimercaptosuccinic acid is dissolved in water by adding a tri-($C_{1-3}$)alkylamine to a pH value of at least 8.

10. A process as claimed in claim 9 wherein the pH value is from 9 to 11.

11. In a method for the production of a gold decoration on a firing-resistant substrate which comprises applying a gold preparation to the surface of a firing-resistant substrate and subsequently subjecting the substrate to firing, the improvement wherein the gold preparation contains at least one organosulfur gold compound as defined in claim 1.

12. A method according to claim 11, wherein the firing-resistant substrate is a member selected from the group consisting of glass, porcelain and ceramic.

* * * * *